United States Patent [19]

Takagi

[11] Patent Number: 4,874,456
[45] Date of Patent: Oct. 17, 1989

[54] VACUUM DRUM APPARATUS FOR PROVIDING SANITARY ARTICLES

[75] Inventor: Katsumasa Takagi, Yokohama, Japan
[73] Assignee: Koyo Disposable Goods Company, Japan
[21] Appl. No.: 196,622
[22] Filed: May 19, 1988
[51] Int. Cl.$^4$ .................. B29C 51/10; B29C 51/22; B29C 51/36; B29C 51/42
[52] U.S. Cl. .................. 156/471; 53/559; 156/301; 156/498; 156/552; 425/388
[58] Field of Search ............. 156/473, 276, 300, 301, 156/302, 383, 470, 471, 552, 209, 213, 292, 468, 498; 425/83.1, 388; 53/559, 560, 574; 264/545, 547, 555, 556, 571

[56] References Cited

U.S. PATENT DOCUMENTS

| | | | |
|---|---|---|---|
| 1,481,866 | 1/1924 | Heist | 156/292 X |
| 2,888,787 | 6/1959 | Cloud | 53/511 X |
| 2,902,718 | 9/1959 | Martelli et al. | 425/388 X |
| 2,935,828 | 5/1960 | Mahaffy et al. | 53/511 |
| 3,044,117 | 7/1962 | Alspach et al. | 425/388 X |
| 3,091,808 | 6/1963 | Dakin | 53/559 X |
| 3,353,329 | 11/1967 | Cloud et al. | 53/559 X |
| 3,931,383 | 1/1976 | Erlewine et al. | 264/555 X |
| 4,016,628 | 4/1977 | Kolbach | 19/148 |
| 4,119,450 | 10/1978 | Bianco | 156/276 X |
| 4,576,669 | 3/1986 | Caputo | 425/388 X |
| 4,678,527 | 7/1987 | Ulman | 156/251 X |

Primary Examiner—Michael W. Ball
Assistant Examiner—Steven D. Maki
Attorney, Agent, or Firm—Lorusso & Loud

[57] ABSTRACT

Method and apparatus for producing sanitary articles having a body contact layer of a body fluid permeable sheet, an absorptive pad and a cover layer of a body fluid impermeable sheet are disclosed. The apparatus includes a drum having a stationary flange and a rotatable drum portion. A plurality of dies are mounted on the circumferential surface of the rotable drum in a side-by-side relationship. A strip of fluid impermeable sheet is wound around about half of the circumference of the rotary drum. As the rotary drum rotates, the fluid impermeable sheet is forced by fluid pressure into the cavities of the dies, deforming the sheet to form pockets therein for receiving the absorptive pads. The fluid permeable sheet is brought into contact with the fluid impermeable sheet near the bottom of the drum while introducing absorptive members into the formed pockets. The superposed sheets are thermally fused together by means of a heat seal roller. After completion of thermal fusing of the sheets with the absorptive members encased in the pockets, the bonded sheets are transferred to a cutter for successively separating the sanitary articles.

17 Claims, 6 Drawing Sheets

VACUUM DRUM APPARATUS FOR PROVIDING SANITARY ARTICLES

BACKGROUND OF THE INVENTION

The present invention relates to a method of producing sanitary articles such as disposable diapers or the like for absorbing body fluids and an apparatus for carrying out the method, more particularly to method and apparatus for producing sanitary articles with improved efficiency.

Sanitary articles used for absorbing body fluids include articles relating to birth, milk wiping materials, diapers, urine absorbing articles, supporters for various parts of the human body, wound bandages, and bandages for ear, nose or other appendages of the human body. The main requirements for such sanitary articles include (1) the ability to maintain close contact with a complicated anatomical shape without displacement, (2) ease of absorption of excrement, blood, body fluids and secretions, (3) the ability to absorb shock and (4) air permeability.

Figure 6:
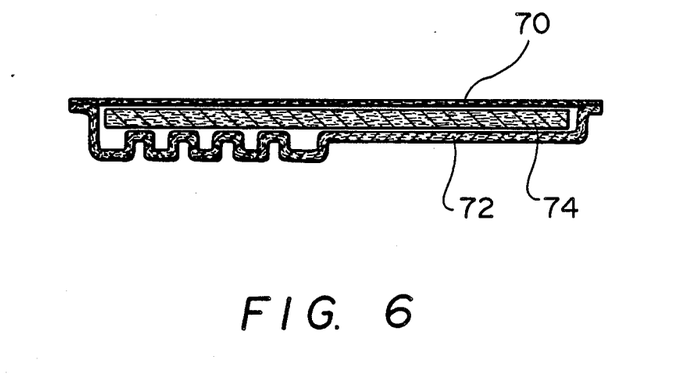
FIG. 6 is a vertical sectional view showing an example of a conventional sanitary article produced in accordance with the present invention.
Figure 7:
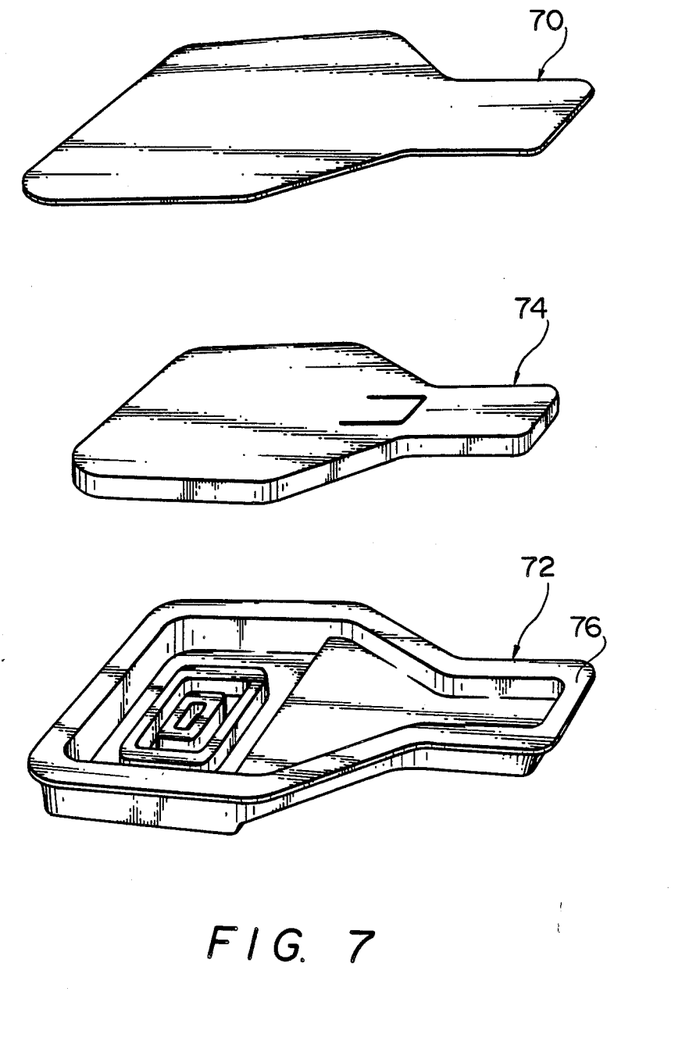
FIG. 7 is an exploded perspective view of the sanitary article shown in FIG. 6.

Typical of a sanitary article which satisfactorily meets these requirements is a paper diaper as illustrated in FIG. 6 which is a cross-sectional view and FIG. 7 which is an exploded perspective view. This sanitary article is usually layered, for example a layered structure having three layers including a body contact layer 70, a receptacle-shaped cover 72 for preventing body fluid from permeating into underclothing or the like and an absorptive pad 74 encased in a hollow space as defined therebetween for absorbing a body fluid.

In order to assure that body fluid will permeate through the contact layer 70, a thermally bonded fibrous body fluid permeable material such as paper, unwoven fabric or the like is used for the contact layer 70. A highly absorptive material such as water absorbing paper, cotton-like pulp or the like is used as the absorptive pad 74. For the cover 72, a thermally fusible and body fluid impermeable material such as foamed polyethylene, foamed polypropylene or the like is employed in order to prevent body fluid from permeating into underclothing or the like.

In general, the cover 72 is shaped as a receptacle so as to accommodate the absorptive pad 74 in a hollow space. The cover 72 has a peripheral flange 76 formed integral therewith, and the contact member 70 and the flange 76 are thermally fused to one another to encase the absorptive pad 74 in the receptacle-shaped interior of the cover 72.

A method of producing sanitary articles having three layers is disclosed in U.S. Pat. No. 4,678,527 issued to John Ulman. According to the Ulman patent, a strip of thermally fusible and body fluid permeable sheet material and a strip of thermally fusible and body fluid impermeable sheet material are moved in parallel with one another at the same speed and a plurality of absorptive pads spaced by a fixed distance are positioned between the strips. Both the sheet strips are wider than the absorptive pads. Thereafter, the strips are thermally fused to one another with the use of a pair of pressing and heating tools in such a manner that the absorptive pads are encased therebetween. Thereafter, the thus assembled material is cut around the periphery of each encased absorptive pad. Thus, the cuts are made in areas where the two sheets are thermally fused together to produce the finished sanitary articles.

The method of the Ulman patent offers the advantage that sanitary products can be produced by successive steps with high productive efficiency. However, due to the fact that two sheet strips are thermally fused in such a manner as to surround a plurality of absorptive pads, it follows that the finished products cannot maintain a constant configuration. In other words, the prior art sanitary article tends to deform during usage and to be displaced from the position where it is applied.

To obviate the foregoing problem, a method producing discrete absorbent cores which assure that sanitary articles maintain a predetermined configuration at all times was proposed by U.S. Pat. No. 4,592,708 issued to Feist et al. According to the Feist et al invention, a drum is formed with a plurality of cavities on its peripheral surface, each of which has a configuration identical to that of the core to be produced, and fibers serving as raw material for the core are injected into each cavity at a high speed. A vacuum is maintained in the interior of the drum in order to prevent the fibers from falling off during rotation of the drum. Thereafter, excess fiber is cut off by means of a scraping roll or cutting cylinder whereby a core having a required shape is obtained. Finally, the core is removed from the drum against the effect of negative pressure by an air jet emanating from a blow-off nozzle.

The method of the Feist et al patent is intended to produce only absorbent cores adapted to maintain a predetermined configuration for sanitary articles. However, uniformity in the step of scraping or cutting the fibers is difficult or impossible to achieve. Further, since the method of the patent is intended to produce only absorbent cores as mentioned above, sanitary articles cannot be produced in closely related successive steps, resulting in lower production efficiency.

As will be readily apparent from the above description, the conventional methods for producing sanitary articles all have drawbacks. Where sanitary articles are produced in successive steps with high production efficiency a stable configuration cannot be assured, whereas where covers of a configuration resisting collapse are produced, they cannot be produced with uniformity and moreover production efficiency is low.

SUMMARY OF THE INVENTION

The present invention has been made with the foregoing background in mind and with the objective of providing method and apparatus for producing sanitary articles automatically in a succession of steps with a low production cost per piece.

To accomplish the above objective, the present invention utilizes (1) a sheet strip of a body fluid permeable material adapted to contact the human body, (2) a sheet strip of a thermally deformable, body fluid impermeable material for producing covers for preventing body fluid from permeating into underclothing or the like and (3) a plurality of absorptive pads in which body fluid is absorbed and retained. The strip of fluid permeable sheet for body contact and the strip of fluid impermeable sheet for the covers are thermally fused or adhered to one another in such a manner that the absorptive pads are encased in a plurality of pockets defined between the two strips.

More specifically, in accordance with the present invention the strip of fluid impermeable sheet is heated to an elevated temperature at which it becomes deformable, and at that elevated temperature is shaped to form a series of spaced pockets suitable for receiving the absorptive pads. These pockets are formed by drawing the strip of the heated fluid impermeable sheet into the interiors of a series of cavities, i.e. in dies, under an effective negative pressure (vacuum). A plurality of absorptive pads are spaced along a strip of a fluid permeable sheet and are brought into registration with the pockets formed in the strip of fluid impermeable sheet to encase the absorptive pads in those pockets by thermally fusing or adhering the two superposed sheets together around the periphery of each pocket. The finished sanitary articles are formed by making successive cuts across the width of the assembled laminate strip in the bonded area between adjacent pockets.

Further, there is provided according to another aspect of the present invention an apparatus for producing sanitary articles by the method outlined above. The apparatus includes heating means for heating the fluid impermeable sheet up to an elevated temperature at which it becomes deformable and a drum formed of a stationary flange and a rotary drum portion around which a plurality of dies are provided in an equispaced relationship. Each of the dies has a cavity of a shape corresponding to a pocket for encasing an absorptive pad. The apparatus further includes means for transfering the fluid impermeable sheet while the latter is wound around the rotary drum, means for drawing the heated fluid impermeable sheet into the interiors of the die cavities and means for feeding the fluid permeable sheet with a plurality of absorptive pads placed thereon so that the fluid impermeable sheet is superimposed on the fluid permeable sheet in such a manner that each absorptive pad is covered by a pocket. Means for thermally fusing or adhering the sheets together to form a seal surrounding each pocket and absorptive pad, and means for severing the thus assembled elements to separate the encased absorptive pads are also provided.

The strip of fluid impermeable sheet is wound around about half of the circumference of the rotary drum. Five stations or positions on the circumference of the drum are important here. At a first position, the fluid impermeable sheet makes contact with and starts to be wound around the rotary drum. The fluid impermeable sheet is partially deformed toward the interior of the die cavity under the effect of a comparatively low intensity negative pressure as it approaches the second position. At the second position, the impermeable sheet is drawn completely to the bottom of the die cavity under a comparative high intensity of negative pressure whereby the fluid impermeable sheet is deformed to a configuration identical that of the die cavity. At the third position, the deformed sheet is still subjected to a comparatively low intensity of negative pressure so as to inhibit the deformed sheet from falling away from the die cavity due to dead weight of the sheet. At the fourth position located proximate the bottom of the rotary drum, absorptive pads are successively introduced into the pockets formed in the fluid impermeable sheet and at the same time the strip of fluid permeable sheet is brought into contact with the strip of fluid impermeable sheet whereby an assembly having the absorptive member encased therein is built. At the fifth position, the superposed sheets with the absorptive pads encased therebetween leave the rotary drum and are transferred to a cutter which separates the assembly into the finished sanitary articles.

The comparatively low intensity vacuum may be conveniently generated by a blower, while the comparatively high intensity vacuum may be conveniently generated by a rotary pump.

A plurality of air suction spaces adapted to be closed by the dies are formed on the outer peripheral surface of the rotary drum. Each of the air suction spaces communicates with the die cavity via air suction holes extending through the die and with a vacuum source. A coolant circulating pipe is provided in the interior of each of the air suction spaces so as to cool the fluid impermeable sheet.

A conveyor for transfering the fluid permeable sheet is arranged near the bottom of the rotary drum and a plurality absorptive pads are successively placed on the moving upper run of the conveyor with equal spacing.

Other objects, features and advantages of the present invention will become readily apparent from a reading of the following description which has been made with reference to the accompanying drawings.

BRIEF DESCRIPTION OF THE DRAWINGS

The present invention will be illustrated in the following drawings in which.

DESCRIPTION OF THE PREFERRED EMBODIMENT

Now, the present invention will be described in a greater detail with reference to the accompanying drawings which illustrate one preferred embodient.

Figure 1:
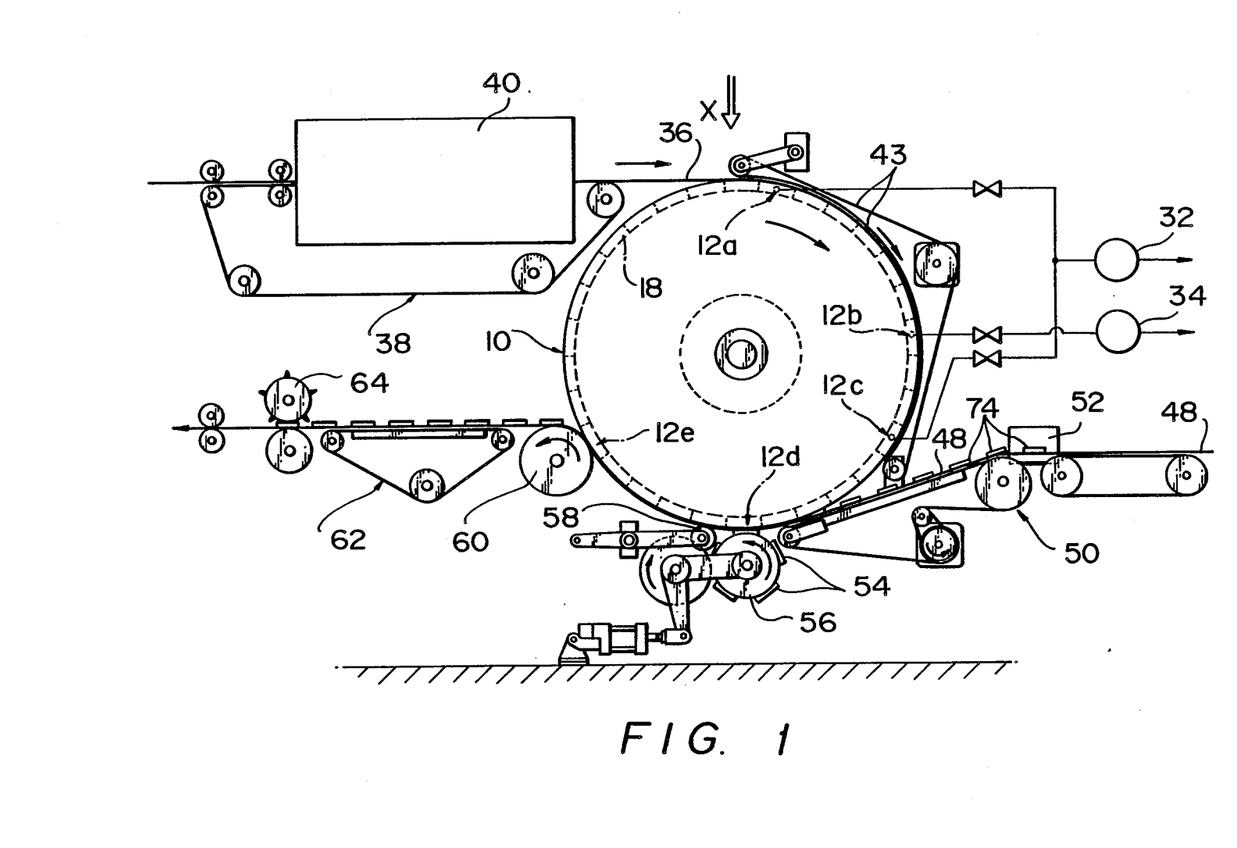
FIG. 1 is a schematic front view of an apparatus for producing sanitary articles in accordance with an embodiment of the present invention.
Figure 3:
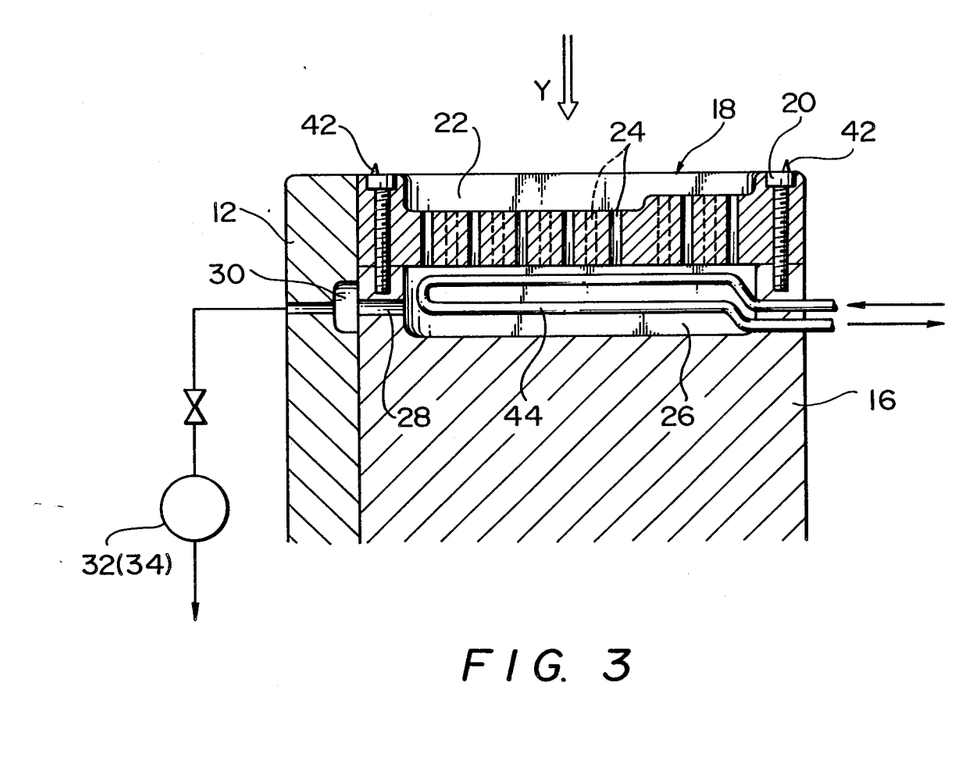
FIG. 3 is an enlarged sectional view of one of the dies mounted on the periphery of the rotary drum shown in FIG. 1.

FIG. 1 provides an overall view of the appratus and method for producing sanitary articles which constitute the present invention. Central to the apparatus is a drum 10 which is supported for rotation in a conventional manner by means which is not shown in the drawings. As seen in FIG. 3 the drum 10 includes a stationary flange 12 and a rotary drum 16 adapted to be rotationally driven by a motor 14 which is mounted on the stationary flange 12. A number of forming dies 18 cover the entire peripheral surface of the rotary drum 16 and are held in place by means of bolts 20.

Each of the dies 18 is formed with a cavity 22 at the central part of the outward facing surface of a shape corresponding to that of cover 72 of the sanitary article shown in FIGS. 6 and 7. Further, each die 18 is formed with a number of air holes 24 which extend between the outer forming surface within cavity 22 to the rear surface of the die. A number of vacuum header spaces 26 adapted to be closed by the dies 18 are formed on the outer peripheral surface of the rotary drum 16. Each of the vacuum header spaces 26 communicates with the cavity 22 via the air suction holes 24. A vacuum passage 28 extends from the air suction space 26 to the face of the rotary drum 16 in contact with the stationary flange 12.

Figure 4:
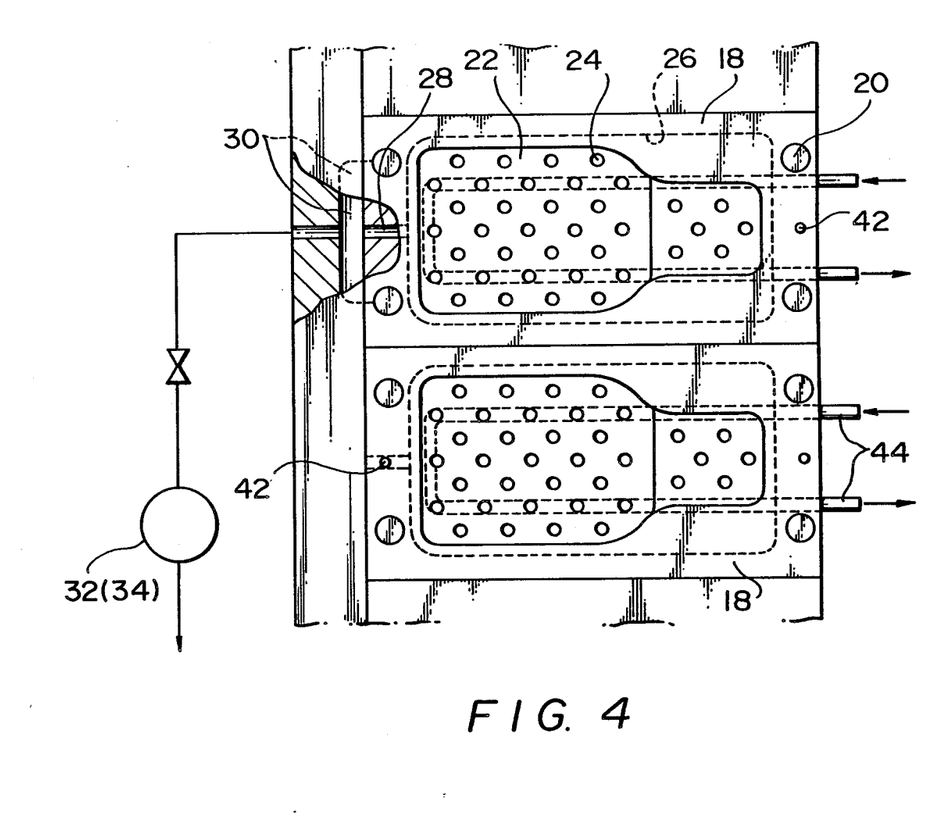
FIG. 4 is a plan view of two dies arranged in a side-by-side relationship as viewed from the direction identified by an arrow "Y" in FIG. 3.

As shown in FIGS. 1, 3 and 4, the stationary flange 12 is formed with three vacuum grooves 30 arranged in three spaced positions 12a, 12b and 12c on the face of the flange 12 which is flush against rotary drum portion 16. These grooves 30 communicate with air suction passages 28 in the rotary drum 16 at a first position 12a located in the proximity of the top of drum 10, a second position 12b spaced from the first position 12a by an angle of about 70 degrees and a third position 12c spaced away from the first position 12a by an angle of about 120 degrees. The air suction grooves 30 located at the first position 12a and the third position 12c communicate with the suction side of a blower 32, which also performs another function as described below, whereby a first negative pressure is established in the air suction grooves 30. On the other hand, the air suction groove 30 located at the second position 12b communicates with the suction side of a rotary pump 34 which is designed and constructed to generate a second negative pressure lower than the negative pressure produced by blower 32. Consequently, a higher degree of vacuum is established in the air suction groove 30 located at the second position than that established in the air suction grooves 30 located at the first and third positions 12a and 12c.

As shown in FIG. 1, an endless belt 38 feeds the drum 10 with a strip of material 36 for forming covers 72, as shown in FIG. 6. A far-infrared ray heating unit 70 is also provided upstream of the drum 10. The strip of material 36 is heated in the heating unit 40 to an elevated temperature at which it becomes deformable and it is then fed to the drum 10 with the aid of the transfer belt 38. In order to heat the sheet 36 up to a proper, predetermined temperature within a short period of time, the heating unit 40 may optionally heat in a plurality of stages. It should be noted that the transfer belt 38 is driven at the same linear speed as the periphery speed of the rotary drum 16 by means of the motor 14.

The sheet 36 is wound around approximately half the circumference of the rotary drum 16, with contact extending from the first position 12a located proximate the top to a fourth position 12d proximate the bottom of the rotary drum 16, whereby the upper surfaces of the dies 18 mounted on the periphery of the rotary drum 16 within that area of contact are covered with the sheet 36. As shown in FIG. 3 and FIG. 4, two upwardly projecting pins 42 are provided on opposite sides of the upper surface of each of the dies 18 so that they impale the sheet 36 so as to prevent the sheet 36 from shifting on the surface of the rotary drum 16 in a manner which might otherwise frustrate the intended objective of thermal deformation.

When the sheet 36 reaches the first position 12a where it starts to wind around the rotary drum 16, the relatively low intensity vacuum is established within the air suction space 26 on the rotary drum 16 by operation of the blower 32, and the vacuum is transmitted to the cavity 22 in the die 18 via the air suction holes 24. The sheet 36 which has been heated up to an elevated temperature at which it becomes deformable is brought into close contact with the outer surfaces of the dies 18 by the thus generated vacuum. Since the suction force produced by the blower 32 is weak, the sheet 36 over the cavity 22 enters only partially into the interior of the cavity 22. In other words, the sheet 36 is subjected to preliminary forming at the first position 12a.

Next, when the sheet 36 reaches the second position 12b, a higher intensity of negative pressure generated by the rotary pump 34 is transmitted to the cavity 22 of the die 18 and the sheet 36 is thereby drawn deeper into the interior of the cavity 22 under the effect of the negative pressure until it comes into close contact with the inner surface of the cavity 22. In other words, the sheet 36 is completely formed at the second position 12b.

Thereafter, at the third position 12c, a lower intensity of negative pressure generated by the blower 32 is exerted on the sheet 36 but this negative pressure functions merely to prevent the formed sheet 36 from hanging down due to dead weight of the sheet 36. An endless belt 43 presses against the surface of rotary drum 16 between the first position 12a and the third position 12c forcing the sheet 36 into tight contact with the peripheral surface of the rotary drum 16 in order to prevent the sheet 36 from separating from the rotary drum 16.

Figure 2:
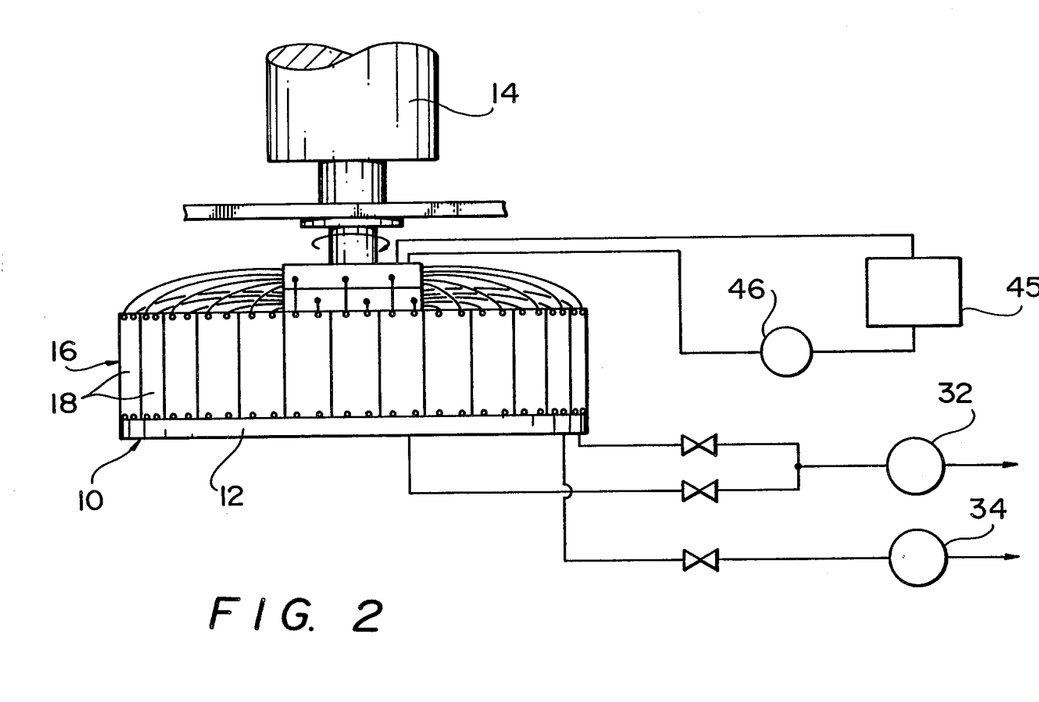
FIG. 2 is a plan view of the apparatus as viewed in the direction identified by an arrow "X" in FIG. 1.

As shown in FIG. 3, a coolant circulating pipe 44 is provided in the interior of each of the air suction spaces 26 formed on the outer peripheral surface of the rotary drum 16. As shown in FIG. 2, coolant is introduced into the coolant circulating pipe 22 from a coolant pump 46 via a coolant tank 45 as a constant flow whereby the rotary drum 16 itself and the sheet 36 wound around the rotary drum 16 are cooled by indirect heat exchange. This results in the sheet 36 being completely cooled before it reaches the fourth position 12d at the bottom of the drum 10. Thus, when the sheet 36 has reached the fourth position 12d, it has formed therein a succession of shaped pockets 72 having the same configuration as that of the cavities 22, arranged in an equally spaced linear relationship.

A conveyor 50 feeds a strip 48, providing contact layer 70, tangentially onto the surface of rotary drum 16 at a point located in the proximity of the fourth position 12d at the bottom of the drum 10.

Unit 52 feeds water absorptive pads 74 onto the sheet 48 with constant spacing onto the sheet 48. As seen in FIG. 1, unit 52 is located to the side of the conveyor 50. The constant distance between the adjacent water absorptive pads 74 is identical to the distance between the adjacent cavities 22 on the outer peripheral surface of the rotary drum 16.

With a number of water absorptive pads 74 placed on the sheet 48 in an equally spaced relationship, the sheet 48 is brought in contact with the sheet 36 wound around the rotary drum 16 at a point located in the proximity of the fourth position 12d at the bottom of the drum 10. Each water absorptive pad 74 placed on the sheet 48 is thereby introduced snugly into a recess formed in the sheet 36 by the cavity 22 of the die 18 slightly before the sheet 48 contacts the sheet 36.

Figure 5:
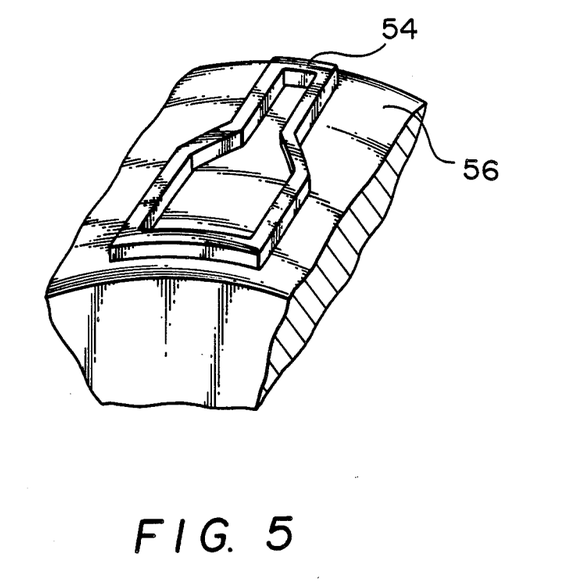
FIG. 5 is a fragmented enlarged perspective view of a heat seal roller shown in FIG. 1.

A heat seal roller 56 carries a plurality of frame-shaped projections 54 circumscribing an area larger than that of a cavity 22 (see FIG. 5). The heat seal roller 56 is positioned below the fourth position 12d on the drum 10. The sheet 36 is thermally fused to the sheet 48 with the aid of the heat seal roller 56 with the water absorptive pad 74 encased within the interior of the thermally fused structure. Of course, the rotational speed of the heat seal roller 56 is set so that the frame-shaped projection 54 correctly contacts rotary drum 16 around the periphery of the cavity 22 on the die 18.

A retaining roller 58 is disposed downstream and adjacent to the heat seal roller 56. This retaining roller 58 is intended to prevent the fused assembly, including sheets 36 and 48 from breaking contact with the surface of the rotary drum 16.

The fused assembly of the sheets 36 and 48 is removed from the rotary drum 16 at a position 12e located remote from the fourth postion 12d and is received on a conveyor 62 via a roller 60. A cutter 64 for cutting the fused assembly of the sheets 36 and 48 around the periphery of each pad 74 is provided at the terminal end of the conveyor 62 for cutting the laminate strip to produce the finished sanitary articles. After completion of cutting operation, the finished sanitary articles are transferred to a packing station by a conveyor (not shown) disposed downstream of the cutter 64.

While the present invention has been described above with respect to a single preferred embodiment thereof, it should be noted that it should not be limited only to this but various changes or modifications may be made in a suitable manner without departure from the spirit and scope of the invention as defined by the appended claims.

What is claimed is:

1. An apparatus for producing sanitary articles having absorptive pads for bodily fluids encased between a body contacting sheet of fluid permeable material and a covering sheet of fluid impermeable material, said apparatus comprising:
   heating means for heating the fluid impermeable sheet to a temperature where it is deformable;
   a drum including a stationary flange having vacuum source port means and a rotary drum portion and a plurality of dies with open cavities facing outward provided on the circumferential surface of the rotary drum member, each of said cavities providing a forming surface therein;
   a plurality of pins, provided on opposite sides of the circumferential surface of said rotary drum member, for impaling and holding in place the edges of the strip of fluid impermeable material;
   first transfer means for feeding the strip of fluid impermeable sheet onto the rotating surface of said rotary drum member;
   vacuum means communicating with said vacuum source port means and for applying a relatively low degree of vacuum and, in sequence, a relatively high degree of vacuum to each cavity to force the heated impermeable sheet into each cavity, against the forming surface therein, and to thereby form pockets in said impermeable sheet;
   means for placing a plurality of the absorptive pads along a length of a strip of the fluid permeable sheet material with equal spacing between the pads;
   second transfer means for feeding a strip of the fluid permeable sheet material into contact with the rotating drum with the pads resting on the fluid permeable sheet coming into registration with said die cavities so that one pad is placed within each pocket formed within the strip of fluid impermeable material;
   sealing means for sealing said strip of fluid impermeable material to said strip of fluid permeable material around the periphery of each of the absorptive pads; and
   severing means for separating the assembled strips between adjacent absorptive pads to form the sanitary articles.

2. The apparatus of claim 1 further comprising cooling means for cooling the strip of fluid impermeable material after formation of the pockets.

3. The apparatus of claim 2 wherein said rotary drum member has a plurality of vacuum header pockets formed around its circumference, each of said vacuum header pockets being closed by one of the die members and wherein each die member has a plurality of apertures extending therethrough to provide for fluid communication between the die cavity and the vacuum header pocket.

4. The apparatus of claim 3 further comprising cooling means for cooling the strip on the drum after formation of pockets by deformation and wherein said cooling means comprises a cooling element in each of said vacuum header pockets.

5. The apparatus of claim 1 wherein each of said dies is provided with a plurality of air suction holes opening to the interior of the die cavity and further comprising vacuum passage means within said rotary drum member for providing fluid communication between said air suction holes and a vacuum source.

6. The apparatus of claim 5 wherein said vacuum passage means within said rotary drum member alternately provides fluid communication between the air suction holes within each die member and two different sources, one providing a greater vacuum than the other.

7. The apparatus of claim 1 wherein said vacuum means comprises a plurality of vacuum header spaces provided on the circumferential surface of said rotary drum member, each of said vacuum header spaces being closed by one of said die members;
   a plurality of air suction holes provided through each of said die members for fluid communication between the die cavity and the corresponding vacuum header space formed on the rotary drum member;
   vacuum port means extending from each of said vacuum header spaces to the surface of the rotary drum pressed against said stationary flange;
   said vacuum source port means including at least one vacuum source port formed within said stationary flange for mating with said vacuum port means, in succession, as said vacuum port means come into registration with said vacuum source port as said rotary drum member rotates; and
   means connecting said vacuum source port with at least one vacuum source.

8. Apparatus in accordance with claim 7 having three of said vacuum source ports two of which are connected to a first vacuum source and the third of which is connected to a second vacuum source operating at a higher vacuum than said first vacuum source and wherein said vacuum source ports are arranged in a spaced relationship so that said vacuum port means in the rotary drum member will come into fluid communication with said first vacuum source port, said second vacuum source port and said third vacuum source port, in succession, whereby a relatively low level vacuum is established, followed by establishment of a relatively high level vacuum followed by establishment of a relatively low level vacuum within each of said vacuum header spaces.

9. The apparatus of claim 1 wherein said sealing means comprises a heat sealing roller disposed in a location proximate to the bottom of the rotating drum, said heat sealing roller carrying, on its circumferential surface, at least one frame-shaped projection circumscribing an area around each of said die cavities and contacting each die with the sheet strips and encased absorptive pads interposed there between thereby forming a heat seal around the periphery of each absorptive pad.

10. The apparatus of claim 9 wherein the peripheral speed of the heat seal roller is equal to the peripheral speed of the rotary drum member.

11. The apparatus of claim 1 wherein the linear speed of said second transfer means is equal to the peripheral speed of the rotary drum member so that the absorptive pads carried on the fluid permeable sheet are introduced singly, in succession, into the pockets formed in the fluid impermeable sheet.

12. The apparatus of claim 9 additionally comprising a retaining roller pressing against the circumferential surface of the rotatable drum member, downstream of said heat sealing roller, for holding the heat sealed strips against the surface of the rotatable drum member.

13. The apparatus of claim 1 including a vacuum source comprising a blower for producing said relatively low degree of vacuum and a rotary pump for producing said relatively high degree of vacuum.

14. The apparatus of claim 7 wherein each die member is bolted to the circumferential surface of said rotary drum member, closing one of said vacuum header spaces.

15. An apparatus for producing sanitary articles having absorptive pads for bodily fluids encased between a body contacting sheet of fluid permeable material and a covering sheet of fluid impermeable material, said process comprising:

heating means for heating the fluid impermeable sheet to a temperature where it is deformable;

a drum including a rotary drum portion having a circumferential surface, a stationary flange covering and pressed against a radial face of said rotary drum portion to form a vacuum seal therewith, said stationary flange being radially coextensive with the circumference of said rotary drum portion, and a plurality of cavities facing outward provided on the circumferential surface of said rotary drum portion;

means for rotating said rotary drum portion relative to said stationary flange;

a die providing a forming surface facing outward of said drum, closing each of said cavities to define a vacuum header space within each of said cavities; and at least one air suction hole extending through said die to provide fluid communication between said forming surface and said vacuum header space;

first transfer means for feeding the strip of fluid impermeable sheet onto the rotating surface of said rotary drum member;

vacuum means for forcing the heated impermeable sheet into each die, against the forming surface therein, and for applying a relatively low degree of vacuum and, in sequence, a relatively high degree of vacuum to each cavity, said vacuum means comprising:

vacuum port means including vacuum passages extending from each of said vacuum header spaces to the radial face of the rotary drum pressed against said stationary flange; and at least one vacuum source port formed within said stationary flange for mating with each of said vacuum passages, in succession, as said vacuum passages come into registration with said vacuum source port as said rotary drum portion rotates;

means for placing a plurality of the absorptive pads along a length of a strip of the fluid permeable sheet material with equal spacing between the pads;

second transfer means for feeding a strip of the fluid permeable sheet material into contact with the rotating drum with the pads resting on the fluid permeable sheet coming into registration with said die cavities so that one pad is placed within each pocket formed within the strip of fluid impermeable material;

means for sealing said strip of fluid impermeable material to said strip of fluid permeable material around the periphery of each of the absorptive pads; and severing means for separating the assembled strips between adjacent absorptive pads to form the sanitary articles.

16. The apparatus of claim 15 additionally comprising:

a plurality of pins, provided on opposite sides of the circumferential surface of said rotary drum member, for impaling and holding in place the edges of the strip of fluid impermeable material.

17. The apparatus of claim 15 wherein said vacuum port means comprises a vacuum port extending from each of said vacuum header spaces, along a straight line parallel to the rotary axis of said rotary drum portion, to said radial face of said drum.

* * * * *

UNITED STATES PATENT AND TRADEMARK OFFICE
CERTIFICATE OF CORRECTION

PATENT NO. : 4,874,456

DATED : October 17, 1989

INVENTOR(S) : Katsumasa TAKAGI

It is certified that error appears in the above-identified patent and that said Letters Patent is hereby corrected as shown below:

IN THE CLAIMS:

Col. 8, line 27, before "sources" insert --vacuum--.

Signed and Sealed this

Fourth Day of September, 1990

Attest:

HARRY F. MANBECK, JR.

Attesting Officer

Commissioner of Patents and Trademarks